United States Patent [19]

Blue et al.

[11] Patent Number: 5,906,974
[45] Date of Patent: *May 25, 1999

[54] HEMOGLOBIN THERAPY IN HEMODIALYSIS

[75] Inventors: John Blue, Gurnee; Jan W. Garber, Barrington; Janet C. Gonder; Gary R. Marchand, both of Crystal Lake, all of Ill.; Robert J. Przybelski, Fitchburg, Wis.; Kathleen N. Stern, Lake Zurich, Ill.

[73] Assignee: Baxter International, Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/701,812

[22] Filed: Aug. 21, 1996

Related U.S. Application Data

[63] Continuation of application No. 08/340,987, Nov. 17, 1994, abandoned, which is a continuation-in-part of application No. 08/330,277, Oct. 27, 1994, abandoned.

[51] Int. Cl.⁶ ........................ A61K 38/16; A61K 39/395; A61K 35/14
[52] U.S. Cl. .............................. 514/6; 424/177; 424/101; 530/385
[58] Field of Search ................................ 514/6; 424/177, 424/101; 530/385

[56] References Cited

U.S. PATENT DOCUMENTS

| | | | |
|---|---|---|---|
| 4,001,401 | 1/1977 | Bonsen et al. | 514/6 |
| 4,757,052 | 7/1988 | Markov | 514/23 |
| 5,296,466 | 3/1994 | Kilbourn | 514/6 |
| 5,439,882 | 8/1995 | Feola et al. | |
| 5,480,866 | 1/1996 | Bonaventura et al. | 514/6 |

FOREIGN PATENT DOCUMENTS

| | | |
|---|---|---|
| 657212 | 9/1993 | Australia. |
| 2087504 | 7/1993 | Canada. |
| 9013309 | 11/1990 | WIPO. |
| 9316721 | 2/1993 | WIPO. |
| 9524213 | 9/1995 | WIPO. |

OTHER PUBLICATIONS

Medline Abstract AN 902 21208, Bergonzi et al, 1990.
Amerling et al. Complications During Hemodialysis Clinical Dialysis, Alpelton & Lang, 3rd Edition, pp. 235–267.
Bradley et al. Is Dialysis Hypotension Caused by an Abnormality of Venous Tone? Br. Med. J. (Clin. Res. Ed.), vol. 296, pp. 1634–1637, (abstract), 1988.
Kouw et al. Interstitial Correction of Blood Volume Decrease During Hemodialysis Int. J. Artif. Organs vol. 12, No. 10, pp. 626–631, (abstract), 1989.
Levin et al. Complications During Hemodialysis Clinical Dialysis, pp. 172–197.

(List continued on next page.)

*Primary Examiner*—Keith D. MacMillan
*Attorney, Agent, or Firm*—Senniger, Powers, Leavitt & Roedel

[57] ABSTRACT

Low doses of stroma-free diaspirin cross-linked hemoglobin are administered to patients undergoing hemodialysis, to achieve hemostabilization and avoid hypotensive episodes in susceptible patients. Hemoglobin therapy when implemented prophylactically in hemodialysis also partially obviates the need for further interventions to control circulatory system instability.

26 Claims, 3 Drawing Sheets

OTHER PUBLICATIONS

Lubbecke et al. Plasma Catecholamines and Alpha I–Adrenoceptor Function in Hemodialysis–Associated Hypotension Ren. Fail, vol. 12, No. 4, pp. 257–261, 1990.

Maeda et al. Mechanism of Dialysis–Induced Hypotension ASAIO Trans. vol. 35., No. 3, pp. 245–247, (abstract), 1989.

Mandelbaum et al. Comment on "Baroreceptor, Not Left Ventricular, Dysfunction is the Cause of Hemodialysis Hypotension" Clin. Nephrol., vol. 32, No. 5, p. 23, (abstact), 1989.

Morrissey et al. Atrial Natriuretric Factor in Renal Failure and Posthemodialytic Postural Hypotension Am. J. Kidney Disorders, vol. 12, No. 6, pp. 510–515, (abstract), 1988.

Nakamura et al. The Role of Peripheral Capacitance and Resistance Vessels in Hypotension Following Hemodialysis Am. Heart Journal, vol. 121 No. 4, Part 1, pp. 1170–1177, (abstract), 1991.

Shimoyama et al. Changes in Catecholamine Level in Hypotensive Patients Subjected to Dialysis Nippon Jinzo Gakkai Shi, vol. 31, No. 2, pp. 165–170 (abstract), 1989.

Burhop et al. Effect of Unmodified Stroma–Reduced and Diaspirin Crosslinked Hemoglobin on the Regional Circulation and Systemic Hemodynamics FASEB J., vol. 8, No. 5, Abstract No. 3625, p. A625, 1994.

Estep et al. Diaspirin Crosslinked Hemoglobin (DCLHb): A Review of Cardiovascular and Pharmacologic Properties ISBS 1993 Program and Abstracts, (1 page).

Gulati et al. Diapsirin Cross–Linked Hemoglobin (DCLHb): Involvement of Adrenergic Mechanisms in the Pressor Effect Art. Cells, Blood Subs., and Immob. Biotech., vol. 22, No. 3, pp. 603–612, 1994.

Gulati et al. Effect of Diaspirin Crosslinked and Stroma–Reduced Hemoglobin on Mean Arterial Pressure and Endothelin–1 Concentration in Rats Life Science, vol. 56, No. 17, pp. 1433–1442, 1995.

Halstenson et al. Pharmacologic Profile of Diaspirin Cross–linked Hemoglobin (DCLHb) in Hemodialysis (HD) Patients Journal of American Society of Nephrology, vol. 5, No. 3, Abstract 84P, pp. 451, 1994.

Katsuyama et al. Nitric Oxide Mediates the Hypertensive Resonse to a Modified Hemoglobin Solution (DCLHb) in Rats Art. Cells, Blood Subs., and Immob. Biotech., vol. 22, No. 1, pp. 1–7, 1994.

Malcolm et al. Characterization of the Hemodynamic Response to Intravenous Diaspirin Crosslinked Hemoglobin Solution in Rats Art. Cells, Blood Subs., and Immob. Biotech., vol. 22, No. 1, pp. 91–107, 1994.

Przybelski et al. Clinical Studies with Diaspirin Cross–Linked Hemoglobin Solution (DCLHb): A Review and Update Art. Cells, Blood Subs., and Immob. Biotech., vol. 24, No. 4, p. 407, 1996 (abstract).

Sharma et al. Role of Nitric Oxide in Cardiovascular Effects of Diaspirin Cross–Linked (DCLHb) and Stroma Reduced Hemoglobin (SRHb) FASEB J., vol. 8, No. 5, Abstract No. 3626, p. A625, 1994.

Sharma et al. Regional Circulatory and Systemic Hemodynamic Effects of Diaspirin Cross–Linked Hemoglobin in the Rat Art. Cells, Blood Subs., and Immob. Biotech., vol. 22, No. 3, pp. 593–602, 1994.

Sherman et al. The Effect of Red Cell Transfusion on Hemodialysis–Related Hypotension Am. J. Kidney Dis., vol. 11, No. 1, pp. 33–35, 1988.

Swan et al. Pharmacologic Profile of Diaspirin Cross–Linked Hemoglobin in Hemodialysis Patients American Journal of Kidney Disease, vol. 26, No. 6, pp. 918–923, 1995.

Wyngaarden et al. Cecil Textbook of Medicine W.B. Saunders, 19th Edition, vol. 2, pp. 2162–2165, 1992.

Zietlow An Overview of DCLHb and Blood Substitutes 8th European Congress of Intensive Care Medicine, Greece, pp. 813–816, 1995.

Noris, et al., Enhanced Nitric Oxide Synthesis in Uremia Implications for Platelet Dysfunction & Dialysis Hypotension Kidney Intl., vol. 44, pp. 445–450 (1993).

Lubbecke, et al., Thrombocyte Alpha–2–Adrenoceptors and Hypotension in Hemodialyzed Patients, Nephron, vol. 68, pp. 268–269 (1994).

Fabris, et al., Conflicting Results on Peripheral Adrenoceptor Function in Hypotension of Hemodialyzed, Nephron, vol. 68, p. 270 (1994).

Yokokawa, et al., Nitric Oxide Mediates the Cardiovascular Instability of Haemodialysis Patients, Current Opinion in Nephrology and Hypertension, vol. 5, pp. 359–363 (1996).

Iada, et al., treatment of Dialysis–Inducted Hypotension with L–threo–3,4–dihydroxyphenylserine, Nephrol. Dial. Transplant, vol. 9, pp. 1130–1135 (1994).

HEMOGLOBIN THERAPY IN HEMODIALYSIS

CROSS REFERENCE TO RELATED APPLICATION

This is a continuation of application Ser. No. 08/340,987, filed Nov. 17, 1994, which is a continuation-in-part of now abandoned U.S. patent application Ser. No. 8/330,277 filed Oct. 27, 1994 abandoned.

BACKGROUND OF THE INVENTION

Kidney dialysis has been a therapeutic boon to thousands of patients a year, who have severely compromised or nonexistent kidney function. However, many of these patients experience side effects and complications ranging from hypersensitivity to recurrent hypotension. For a general discussion of hemodialysis complications, see Levin, et al., "Complications During Dialysis", in Nissenson, et al., eds., *Dialysis Therapy,* Hanley & Belfes, Inc., 1986, p. 85. Among the most common of complications is hypotension, arising in 20–30 percent of all hemodialysis patients. Many of these patients experience chronic hypotension, some so severe that they cannot tolerate the procedure at all, and must resort to peritoneal dialysis or transplant. The incidence of intradialytic hypotension occurs most frequently in older patients and in women.

The cause of intradialytic hypotension varies depending on whether it occurs early or late in the treatment phase. It may result when the rate of intravascular volume depletion during ultrafiltration exceeds replacement. The diffusion of replacement fluid into the intravascular space counteracts the normal compensatory response of increased peripheral resistance. Also, hypotension can occur even during volume overload because of the time dependency of refilling of the intravascular space. Similarly, if the patient's weight is below the "dry weight", volume shifts may no longer be adequate to maintain blood pressure. For a discussion of the causes of hypotension in hemodialysis, see Schulman, et al., "Complications of Hemodialysis", in Principles and Practices of Nephrology, Jacobson, et al., eds., B. C. Decker, Inc., 1991, pp. 757–759.

Other causes of intradialytic hypotension have been described. Shulman, infra, p. 759 lists as early hemodialysis hypotension causes: dialyzer volume, bioincompatible membranes, various medications, sepsis, and pericardial tamponade; listed as late stage hypotension causes, in addition to ultrafiltration rate and a too low setting for dry weight: excessive weight gain, decline in osmolarity, acetate accumulation, arrhythmia, and autonomic neuropathy. It is significant to note that most of the common causes of intradialytic hypotension involve fluid volume changes for which the body is incapable of fully compensating.

Treatment of intradialytic hypotension focuses on its suspected cause. If a too rapid removal of fluids is the suspected cause, dialysis is discontinued and the patient is placed in the Trendelenburg position to enhance venous return. (See *Kidney Electrolyte Disorders,* eds. J. C. M. Chan, et al., Churchill Livingstone, 1990). The most common pharmacologic intervention for hypotension is administration of isotonic or hypertonic saline, to restore fluid balance. Pressor agents are not generally recommended, in part because a high percentage of hemodialysis patients are older persons with manifest clinical hypertension. In fact, it is recommended in designing hemodialysis regimens for these patients, that all blood pressure medication be curtailed for at least four hours prior to treatment.

SUMMARY OF THE INVENTION

Since patients requiring hemodialysis generally must be treated two to three times weekly for several hours per treatment, it is medically desirable to minimize complications as much as possible to avoid sequelae requiring further intervention, and needless traumatization of the patient. This is especially desirable for predictably recurrent complications in particular patient subgroups, such as those having recurrent hypotension.

It is therefore an object of the present invention to provide a preventive therapy in which an agent is administered prophylactically about the time dialysis commences, to achieve circulatory stability and maintain blood pressure at acceptable levels. From the standpoint of patient well-being it is preferable to prevent hypotension from occurring than to treat the condition once it is manifest.

It is a further object of the invention to provide a therapy for intradialytic hypotension generally which prevents hypotension arising from multiple causes, and not just treating manifest hypotension once a suspected cause has been identified.

In the method of the present inventions stroma-free hemoglobin is peridialytically administered in a low dose for stabilizing the circulatory system in hemodialysis patients susceptible to chronic episodes of blood pressure fluctuation, and for treating chronic hypotension in susceptible patients undergoing hemodialysis.

The hemoglobin solution administered is stroma-free hemoglobin and preferably diaspirin cross-linked. It is advantageous to administer the solution over a period of 10 to 45 minutes after commencement of hemodialysis.

DETAILED DESCRIPTION OF THE PREFERRED EMBODIMENT

Figure 1:
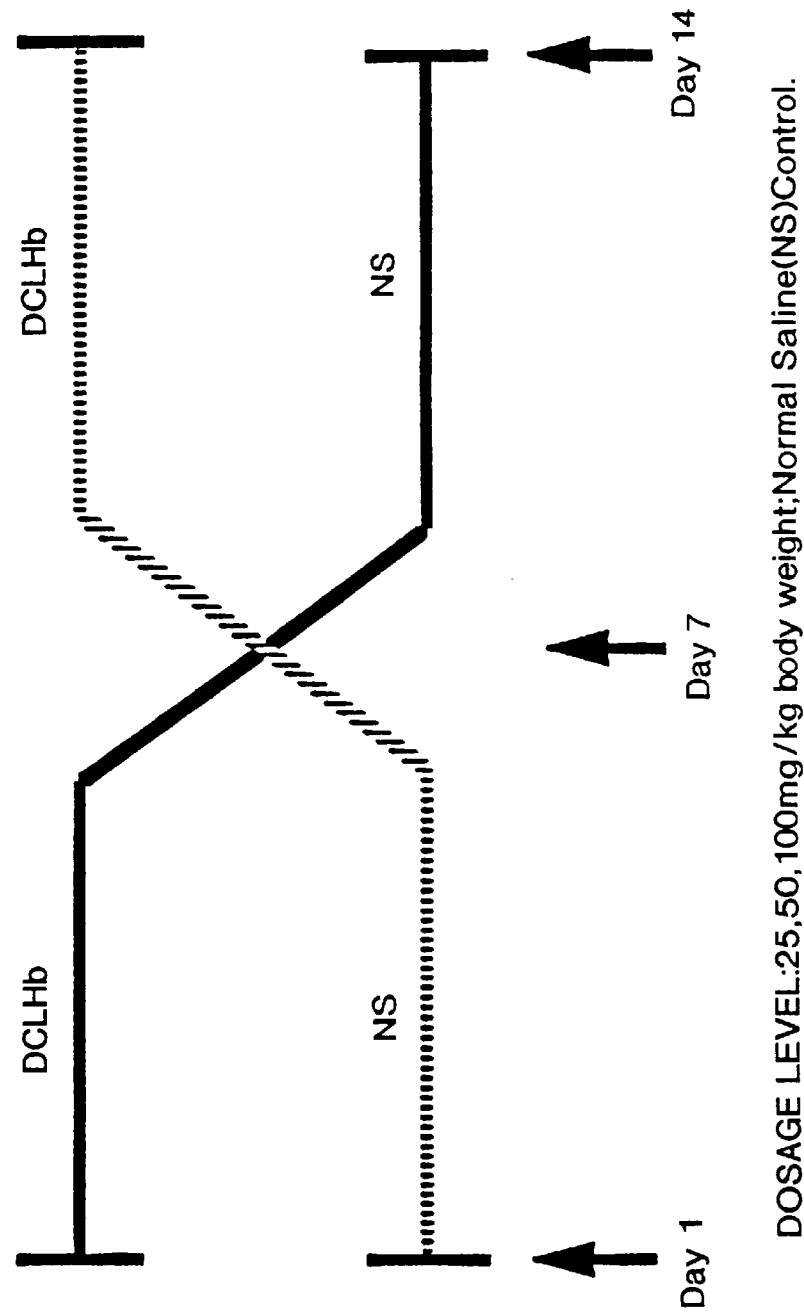
FIG. 1 is a schematic showing the design of clinical trials.

While any patient undergoing renal hemodialysis may encounter complications because of the frequency and duration of treatment, certain patient subgroups appear to be especially prone to complications such as hypotension occurring early in the procedure or in the later stages. These recurrent hypotensive episodes can be generally of two types, (1) in which blood pressure fluctuates, sometimes erratically, or (2) the patient experiences a sudden drop in pressure resulting in dizziness and actual fainting. These episodes may be accompanied by cardiac arrhythmia, which actually contributes to the condition. Such sudden drops in pressure may occur more than once in a single dialysis procedure. In general, a hypotensive event is said to occur when blood pressure falls either suddenly or transiently about 10 minutes after procedure initiation, by greater than about 20 mm Hg, or when systolic blood pressure falls below 100 mm Hg although these criteria will vary and are often interpreted very subjectively.

Patients who experience hypotension or blood pressure fluctuation can be identified from their file histories, and may be considered for the hemoglobin therapy of the present invention if routine adjustments in the dialysis procedure (lowering rate of ultrafiltration, salt concentration of the dialysate, etc.) do not produce a remission of the episodes. It will largely be a matter for the attending physician or nephrologist to ascertain those who qualify for hemoglobin therapy, taking into account factors such as the age and condition of the patient, secondary pathologies, drug regimens, the frequency and severity of hypotensive episodes, etc.

Administration of hemoglobin suppresses blood pressure fluctuation, and largely prevents intradialytic hypotension. One unexpected benefit is to minimize and virtually obviate conventional therapeutic intervention, even for causes of hypotension classically associated with fluid imbalances. Infusions of albumin, iso- and hypertonic saline, are avoided, which enhances patient comfort and well-being during the dialysis procedure.

The hemoglobin therapy of the present invention involves administration of hemoglobin in a pharmacologically effective amount, generally, at low doses. In the clinical studies set forth in the Example, three dose levels of 25, 50 and 100 mg hemoglobin/kg body weight were infused. In other studies, and from animal models, pharmacologic efficacy is achieved in dose ranges from 10 mg/kg to about 1200 mg/kg. Any dose in this range is "low" when defined as an amount of hemoglobin too low to serve as a one-for-one oxygen carrying replacement for whole blood in which blood loss results in hypotension at least as pronounced as is observed in susceptible patients undergoing hemodialysis.

Response of individual patients to particular doses of hemoglobin will vary, as with any drug, and the physician will adjust the dose to achieve the optimal effect. In some patients a dose of 15 mg/kg may be adequate, but in others a dose towards the high end of the recommended dose range (1200 mg/kg) may be required. In the occasional patient a dose in excess of 1200 mg/kg may be needed to be pharmacologically effective, and is still considered by Applicants to be within the scope of the invention so long as the low dose definition set forth herein is met.

While it is known that the pharmacologic effects of hemoglobin are dose dependent up to a certain threshold, the duration of the effects is affected by dose, with the effects obtained at a larger dose continuing longer. In patients having a history of primarily late stage hypotension, larger doses may be indicated so that an adequate level is present at later times in the dialysis treatment, when hypotensive episodes are anticipated. In some patients, it may be most beneficial to administer the hemoglobin in more than one dose, or even in a continuous dose, over the course of dialysis. Such variations are within the scope of the present invention, so long as administration occurs peridialytically in relation to the treatment.

Timing of hemoglobin administration is preferably coincident with the commencement of dialysis, and continues by intravenous infusion over a 10 to 45 minute period. Although hemoglobin administration may be efficacious as a palliative during acute episodes of hypotension, the principal embodiment of the invention is to administer the hemoglobin prophylactically in advance of such episodes so as to prevent hypotensive episodes from occurring.

The hemoglobin utilized in the treatment of this invention is stroma-free, substantially free of endotoxin, and sterile. While unmodified stroma-free hemoglobin is pharmacologically effective, it tends to dissociate readily into its subunits giving it a much reduced half-life in the bloodstream. Renal toxicity has also been reported. It is therefore preferable to utilize a cross-linked, or crosslinked polymerized hemoglobin manufactured according to a number of methods in the art, for example, as described in U.S. Pat. Nos. 4,826,811, 4,001,401, 4,412,989, and 5,084,558. Most preferred is diaspirin cross-linked hemoglobin made as disclosed in U.S. Pat. Nos. 4,600,531 and RE34,271 hereby incorporated by reference. The hemoglobin is further purified and sterilized as disclosed in U.S. Pat. Nos. 4,831,012, 4,861,867, and 5,128,452.

Further advantages of the present invention will be apparent from the Example which follows:

EXAMPLE

Diaspirin cross-linked hemoglobin (DCLHb) in a 10 percent solution was infused into patients undergoing hemodialysis according to the randomized, single-blinded, cross-over protocol illustrated in FIG. 1. Approximately equal numbers of patients (n=3) for a test group and a control group receiving normal saline, for each of 3 treatment groups (25, 50, and 100 mg hemoglobin/kg of body weight) were infused on day 1 with either saline or DCLHb. At day 7 the groups were reversed and then infused with the opposite of either saline or DCLHb than they received on day 1. Since one patient received only the control solution and did not cross-over, an extra patient was added to the control group, bringing the total to 19. Patients were unaware of which treatment was received. Various physiologic parameters were monitored, including blood pressure and the incidence of conventional intervention for hypotension.

Figures 1, 2A:
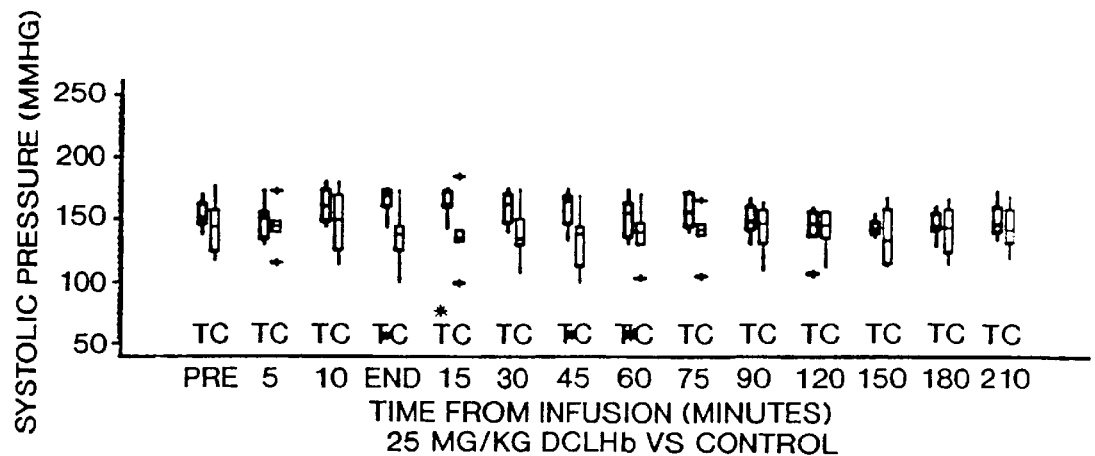
FIGS. 2a and 2b are graphs depicting the course of systolic (2a) and diastolic (2b) blood pressure during hemodialysis.
Figures 2, 2A:
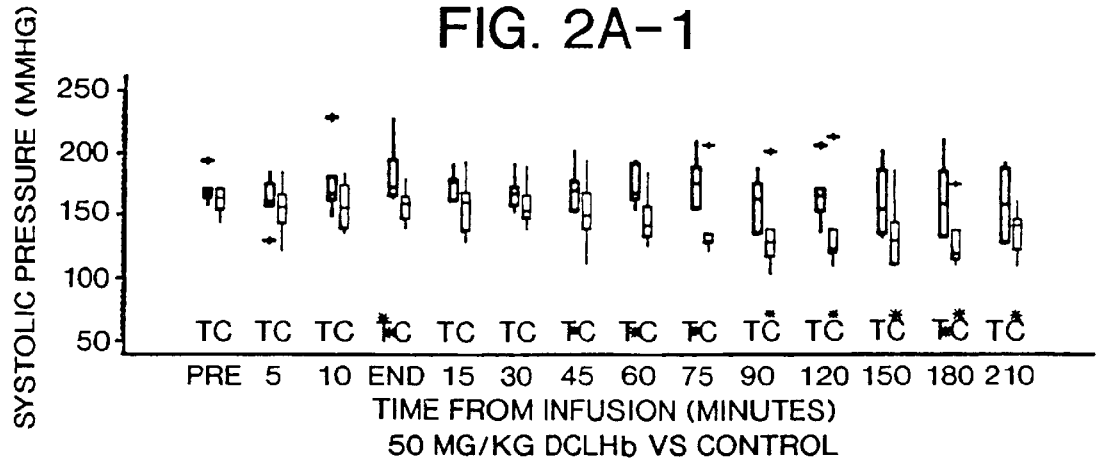
Figures 2, 2A, 3:
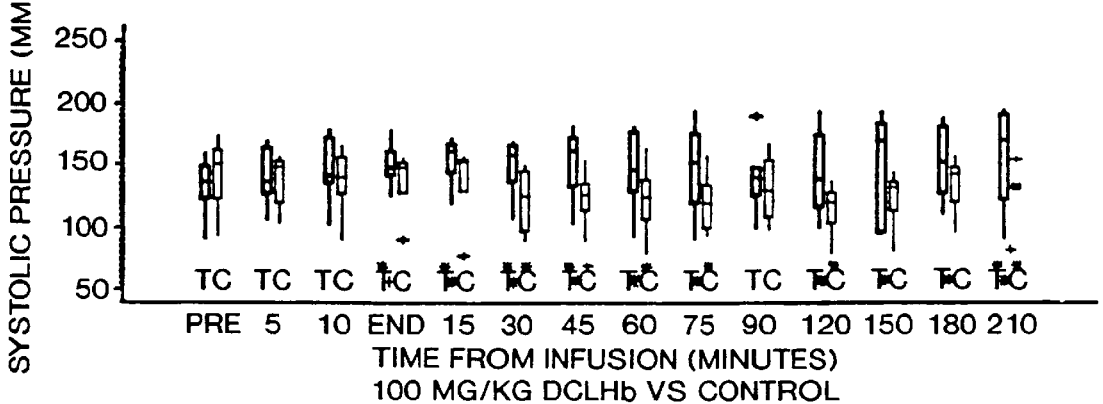
Figures 1, 2B:
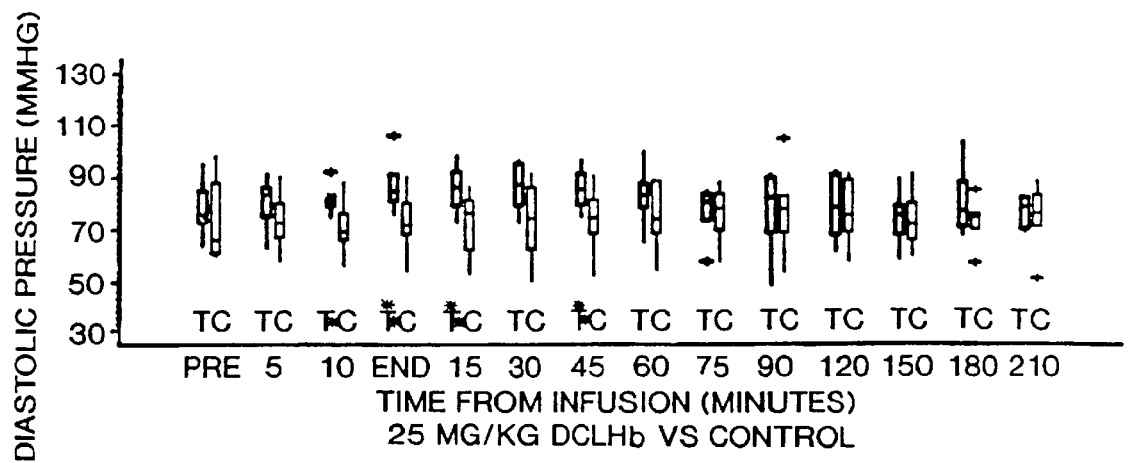
Figures 2, 2B:
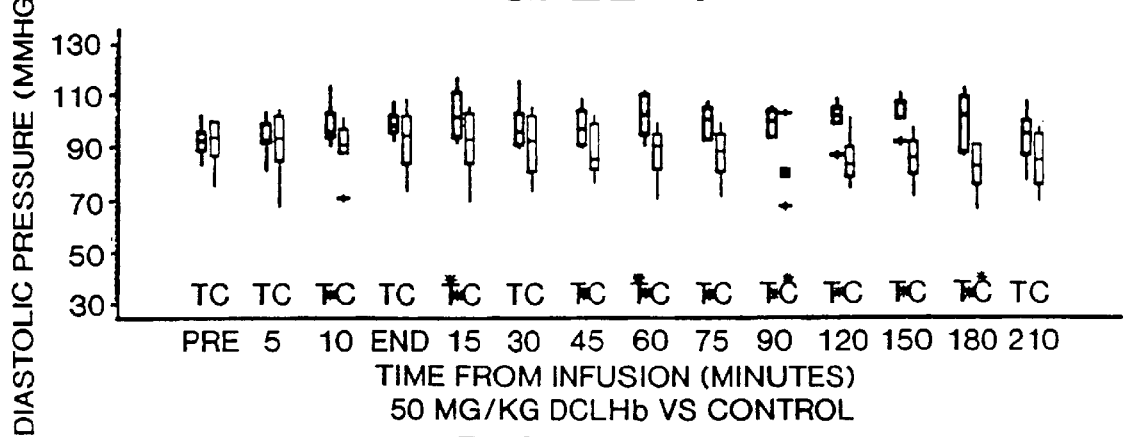
Figures 2, 2B, 3:
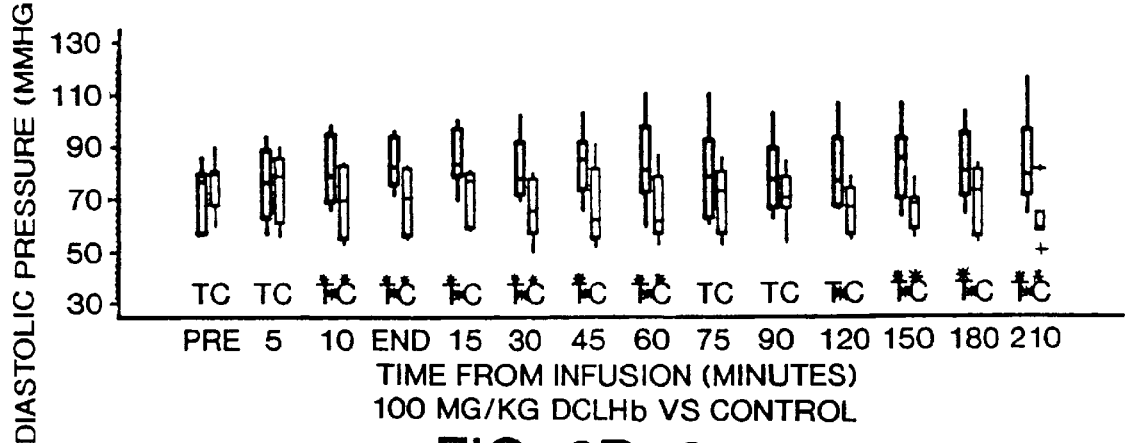

FIGS. 2a and 2b depict the data for systolic and diastolic pressures. It is evident that the test and control groups at each dosage level do not differ at the commencement of dialysis, but thereafter out to about 210 minutes there is a significant elevation in both systolic and diastolic pressures. Thereafter, the groups once again become indistinguishable.

Table 1 summarizes the combined systolic blood pressure data. Blood pressure increases are dose dependent averaging 2 mm Hg for 25 mg/kg dose and 29 mm Hg for the 100 mg/kg group.

TABLE 1

| Blood Pressure Change | 25 mg/kg | 50 mg/kg | 100 mg/kg |
|---|---|---|---|
| Change in BPs DCLHb | 2 ± 12* | 15 ± 29* | 29 ± 8* |
| Change in BPs placebo | −1 ± 9 | 4 ± 10 | −4 ± 12 |

*p < 0.05 vs. placebo; MANOVA

Correspondingly, the control groups generally demonstrated a reduction in systolic blood pressure.

The results in Table 2 indicate an increase in hypotensive events as indicated by increased administration of hypertonic saline. The frequency of hypertonic saline interventions were significantly less in the DCLHb groups.

The stabilization of blood pressure as indicated by the number of hypertonic saline interventions (Table 2) indicates 1 hypotensive episode in one of 18 patients receiving DCLHb compared to 20 episodes in 9 of 19 patients while receiving the control solution. Thus, low dose hemoglobin administration incident to hemodialysis stabilizes blood pressure and significantly reduces the need for conventional hypotensive interventions.

TABLE 2

Frequency of 23.4% NaCl IVP for Treatment or Prevention of Hypotension

| | DCLHb<br># interventions (# patients) | Normal Saline<br># interventions<br>(# patients) |
|---|---|---|
| 25 mg/kg | 1(1) | 3(2) |
| 50 mg/kg | 0(0) | 9(5) |
| 100 mg/kg | 0(0) | 8(2) |
| Total Interventions<br>(Total Patients) | 1(1) | 20(9) |

What is claimed is:

1. A method for reducing the severity of or preventing hypotension in a patient undergoing hemodialysis comprising administering stroma-free hemoglobin to a patient, the hemoglobin being administered before the patient develops hypotension during hemodialysis.

2. The method of claim 1 wherein the hemoglobin is administered when hemodialysis is initiated.

3. The method of claim 2 wherein the hemoglobin administration continues for 10 to 45 minutes after initiation of hemodialysis.

4. The method of claim 1 wherein the patient is a human.

5. The method of claim 1 wherein the stroma-free hemoglobin is selected from the group consisting of crosslinked hemoglobin and polymerized hemoglobin.

6. The method of claim 5 wherein the crosslinked hemoglobin is diaspirin-crosslinked hemoglobin.

7. The method of claim 1 wherein the stroma-free hemoglobin is a physiologically acceptable solution containing from about 10 milligrams hemoglobin per kilogram body weight to about 1,200 milligrams hemoglobin per kilogram body weight.

8. The method of claim 1 wherein the stroma-free hemoglobin is a physiologically acceptable solution containing from about 25 milligrams hemoglobin per kilogram body weight to about 100 milligrams hemoglobin per kilogram body weight.

9. The method of claim 1 wherein the hemoglobin is administered in more than one dose or by continuous infusion.

10. A method for stabilizing the circulatory system of a hemodialysis patient comprising administering stroma-free hemoglobin to a patient susceptible to blood pressure fluctuation during hemodialysis, the hemoglobin being administered before the patient experiences blood pressure fluctuation during hemodialysis.

11. The method of claim 10 wherein the hemoglobin is administered when hemodialysis is initiated.

12. The method of claim 11 wherein the hemoglobin administration continues for 10 to 45 minutes after initiation of hemodialysis.

13. The method of claim 10 wherein the patient is a human.

14. The method of claim 10 wherein the stroma-free hemoglobin is selected from the group consisting of crosslinked hemoglobin and polymerized hemoglobin.

15. The method of claim 14 wherein the crosslinked hemoglobin is diaspirin-crosslinked hemoglobin.

16. The method of claim 10 wherein the stroma-free hemoglobin is a physiologically acceptable solution containing from about 10 milligrams hemoglobin per kilogram body weight to about 1,200 milligrams hemoglobin per kilogram body weight.

17. The method of claim 10 wherein the stroma-free hemoglobin is a physiologically acceptable solution containing from about 25 milligrams hemoglobin per kilogram body weight to about 100 milligrams hemoglobin per kilogram body weight.

18. The method of claim 10 wherein the hemoglobin is administered in more than one dose or by continuous infusion.

19. A method for reducing the severity of or preventing hypotension in a patient undergoing hemodialysis comprising peridialytically administering from about 10 milligrams stroma-free hemoglobin per kilogram body weight to about 1,200 milligrams stroma-free hemoglobin per kilogram body weight to a patient before the patient develops hypotension during hemodialysis.

20. The method of claim 19 wherein the patient is a human.

21. The method of claim 19 wherein the stroma-free hemoglobin is selected from the group consisting of crosslinked hemoglobin and polymerized hemoglobin.

22. The method of claim 21 wherein the crosslinked hemoglobin is diaspirin-crosslinked hemoglobin.

23. A method for stabilizing the circulatory system of a hemodialysis patient comprising peridialytically administering from about 10 milligrams stroma-free hemoglobin per kilogram body weight to about 1,200 milligrams stroma-free hemoglobin per kilogram body weight to a patient before the patient experiences blood pressure fluctuation during hemodialysis.

24. The method of claim 23 wherein the patient is a human.

25. The method of claim 23 wherein the stroma-free hemoglobin is selected from the group consisting of crosslinked hemoglobin and polymerized hemoglobin.

26. The method of claim 25 wherein the crosslinked hemoglobin is diaspirin-crosslinked hemoglobin.

* * * * *

UNITED STATES PATENT AND TRADEMARK OFFICE
CERTIFICATE OF CORRECTION

PATENT NO.    : 5,906,974
DATED         : May 25, 1999
INVENTOR(S)   : John Blue et al.

It is certified that error appears in the above-identified patent and that said Letters Patent is hereby corrected as shown below:

On the title page of the issued patent, section 63, "Continuation of application No. 08/340,987, Nov. 17, 1994, abandoned, which is a continuation-in-part of application No. 08/330,277, Oct. 27, 1994, abandoned." which should read ---Continuation of application No. 08/340,987, Nov. 17, 1994, abandoned---.

Signed and Sealed this

Seventh Day of August, 2001

*Attest:*

*Attesting Officer*

NICHOLAS P. GODICI
*Acting Director of the United States Patent and Trademark Office*